(12) United States Patent
Wang et al.

(10) Patent No.: US 10,201,549 B2
(45) Date of Patent: Feb. 12, 2019

(54) TESTOSTERONE COMBINED WITH ANASTROZOLE INJECTION SOLUTIONS

(71) Applicant: Professional Compounding Centers of America (PCCA), Houston, TX (US)

(72) Inventors: Tsu-I Catherine Wang, Sugar Land, TX (US); Bruce Vincent Biundo, Houston, TX (US)

(73) Assignee: Professional Compounding Centers of America (PCCA), Houston, TX (US)

( * ) Notice: Subject to any disclaimer, the term of this patent is extended or adjusted under 35 U.S.C. 154(b) by 0 days.

(21) Appl. No.: 13/918,323

(22) Filed: Jun. 14, 2013

(65) Prior Publication Data
US 2014/0371186 A1    Dec. 18, 2014

(51) Int. Cl.
*A61K 31/568* (2006.01)
*A61K 47/44* (2017.01)
*A61K 9/00* (2006.01)
*A61K 31/4196* (2006.01)

(52) U.S. Cl.
CPC .......... *A61K 31/568* (2013.01); *A61K 9/0019* (2013.01); *A61K 31/4196* (2013.01); *A61K 47/44* (2013.01)

(58) Field of Classification Search
None
See application file for complete search history.

(56) References Cited

U.S. PATENT DOCUMENTS

| 2003/0232072 | A1  | 12/2003 | Dudley et al. |
| 2005/0042279 | A1* | 2/2005  | De Matas ............ A61K 9/2866 424/464 |
| 2005/0112181 | A1  | 5/2005  | Dudley et al. |
| 2005/0165081 | A1  | 7/2005  | Plourde et al. |
| 2010/0297194 | A1* | 11/2010 | Catron et al. .................. 424/400 |
| 2011/0160168 | A1* | 6/2011  | Dhingra ....................... 514/170 |

FOREIGN PATENT DOCUMENTS

EP    2205239 A2    7/2010

* cited by examiner

*Primary Examiner* — Anna Pagonakis
(74) *Attorney, Agent, or Firm* — David G. Woodral; GableGotwals

(57) ABSTRACT

Compositions and methods for testosterone booster injection solutions (TBIS) that includes testosterone cypionate in synergistic combination with anastrozole are disclosed. Disclosed TBIS may be administered for treating testosterone deficiency. Disclosed TBIS is an intramuscular injection. The therapeutic dosage and protocol varies, according to the individual person. Different formulations may be designed to provide higher or lower testosterone doses.

6 Claims, No Drawings

TESTOSTERONE COMBINED WITH ANASTROZOLE INJECTION SOLUTIONS

CROSS-REFERENCE TO RELATED APPLICATIONS

N/A
N/A

BACKGROUND

Field of the Disclosure

The present disclosure relates in general to compositions and methods for the production of testosterone boosters; more particularly, to injection solutions including testosterone combined with anastrozole.

Background Information

The production of testosterone naturally decreases with age and results in many unwanted physical and mental changes.

In general, doctors prescribe testosterone injections or testosterone topical products for increasing testosterone levels. Testosterone injections have been proved to be the most effective testosterone boosters.

Testosterone is the primary male androgen, playing a vital role in overall male health. Testosterone is essential to the development and maintenance of specific reproductive tissues (testes, prostate, epididymis, seminal vesicle, and penis) and male secondary sex characteristics. Testosterone plays a key role in libido and erectile function and is necessary for the initiation and maintenance of spermatogenesis. Furthermore, testosterone has important functions not related to reproductive tissues. For example, testosterone positively affects body composition by increasing nitrogen retention, which supports lean body mass, muscle size and strength. Testosterone may also act on bone to stimulate bone formation.

There are several benefits to taking a testosterone booster to increase testosterone levels. Some of these benefits include faster muscle growth, weight loss and fat reduction, improved memory, more energy, increased strength and improved stamina. An increase in sex drive and a general improvement in overall health and wellness may be obtained by the administration of testosterone boosters.

Furthermore, there is another substance, called anastrozole that may be employed to increase testosterone levels. Anastrazole is an aromatase inhibitor (AI) that works by binding to the aromatase enzyme that converts testosterone into estrogen. Therefore, anastrozole effectively inhibits or blocks conversion of testosterone into estrogen. There is further evidence that high estrogen levels can cause the pituitary gland to decrease production of Luteinizing hormone (LH), therefore lowering testosterone production.

For the aforementioned reasons, there is a need for compositions and methods for testosterone booster injection solutions that include testosterone and anastrozole synergistically combined.

SUMMARY

Compositions and methods for testosterone booster injection solution (TBIS) that includes testosterone in synergistic combination with anastrozole are disclosed.

The synergistic effect between testosterone and anastrozole may lead to increased levels of testosterone in the patient; therefore, TBIS may be used in treating a wide variety of conditions responsive to testosterone deficiency.

Amount of testosterone cypionate in disclosed TBIS may be of about 5% weight by volume to about 20% weight by volume; most suitable amount may be of about 10% weight by volume to about 20% weight by volume.

Amount of anastrozole in disclosed TBIS may be of about 0.005% weight by volume to about 0.5% weight by volume; most suitable amount may be of about 0.05% weight by volume to about 0.2% weight by volume.

According to an embodiment, a suitable vegetable oil such as Almond oil, Corn oil, Cottonseed oil, olive oil, Peanut oil, Sesame oil, Soybean oil, and medium chain triglycerides (or caprylic capric triglycerides), among others, may be included as solvent within TBIS. Additionally, TBIS may include other suitable solvents such as benzyl alcohol and benzyl benzoate, among others.

TBIS may be produced by suspending or emulsifying APIs in suitable vegetable oil such as Almond oil, Corn oil, Cottonseed oil, Olive oil, Peanut oil, Sesame oil, Soybean oil, and medium chain triglycerides (or caprylic capric triglycerides), among others. Additionally, other suitable solvents such as Benzyl alcohol and benzyl benzoate may be added. TBIS may then be packed in suitable packages. Appropriate aseptic procedures must be observed through the entire process, and suitable sterilization must be done.

In other embodiments, TBIS may be produced into an aqueous injection together with, for example, surfactants, dispersing agent, suspending agents, preservatives, and tonicity adjusting agent, among others.

Disclosed TBIS is an intramuscular injection. The therapeutic dosage and protocol varies, according to the individual person. Different formulations may be designed to provide higher or lower testosterone doses.

TBIS may be administered to a patient in weekly doses that results in a pharmacologically effective blood concentration of testosterone over a suitable period of time. The dosage may be of from about 25 mg/week to about 500 mg/week of testosterone; and of from about 0.1 mg/week to about 5 mg/week of anastrozole. Most suitable dosage may be of from about 50 mg/week to about 100 mg/week of testosterone; and of from about 0.1 mg/week to about 5 mg/week of anastrozole. In one embodiment, TBIS may be injected for an undetermined extended period of time. In other embodiments, TBIS may be injected as prescribed by a doctor, according to the patient's need.

Numerous other aspects, features of the present disclosure may be made apparent from the following detailed description.

DETAILED DESCRIPTION

The present disclosure is here described. Other embodiments may be used and/or other changes may be made without departing from the spirit or scope of the present disclosure. The illustrative embodiments described in the detailed description are not meant to be limiting of the subject matter presented here.

DEFINITIONS

As used here, the following terms may have the following definitions:

"Testosterone booster" refers to hormone replacement therapy used to increase testosterone levels.

"Treating" and "Treatment" refer to reduction in severity and/or frequency of symptoms, elimination of symptoms and/or underlying cause, prevention of the occurrence of symptoms and/or their underlying cause, and improvement or remediation of damage.

"Active Pharmaceutical Ingredient" or "API" refers to a chemical compound that induces a desired effect, and includes agents that are therapeutically effective, prophylactically effective, or cosmeceutical effective.

"Vehicle" refers to a substance of no therapeutic value that is used to convey an active medicine for administration.

DESCRIPTION

Embodiments of the present disclosure may be directed towards compositions and methods for producing testosterone booster injection solution (TBIS) that combines testosterone with anastrozole in order to treat testosterone deficiency.

Formulation

TBIS may include testosterone and anastrozole as active pharmaceutical ingredients (APIs) with suitable solvents.

According to an embodiment, a suitable vegetable oil such as Almond oil, Corn oil, Cottonseed oil, Olive oil, Peanut oil, Sesame oil, Soybean oil, and Medium chain triglycerides (or caprylic capric triglycerides), among others, may be included as solvent within TBIS. Additionally, TBIS may include other suitable solvents such as benzyl alcohol and benzyl benzoate, among others.

In some embodiments, various additives, known to those skilled in the art, may be included in TBIS to facilitate the preparation.

APIs

Testosterone

In one embodiment, testosterone within TBIS may be testosterone cypionate which is the oil-soluble 17 (beta)-cyclopentylpropionate ester of the androgenic hormone testosterone.

The chemical name for testosterone cypionate is androst-4-en-3-one, 17-(3-cyclopentyl-1-oxopropoxy)-, (17β)-. The molecular formula of testosterone cypionate is $C_{27}H_{40}O_3$.

Testosterone is the primary male androgen, playing a vital role in overall male health. Testosterone is essential to the development and maintenance of specific reproductive tissues (testes, prostate, epididymis, seminal vesicle, and penis) and male secondary sex characteristics. Testosterone plays a key role in libido and erectile function and is necessary for the initiation and maintenance of spermatogenesis. Testosterone also has important functions not related to reproductive tissues. For example, testosterone positively affects body composition by increasing nitrogen retention, which supports lean body mass, muscle size and strength. Testosterone may also act on bone to stimulate bone formation.

Testosterone deficiency can result from underlying disease or genetic disorders and is also frequently a complication of aging. For example, primary hypogonadism results from primary testicular failure. In this situation, testosterone levels are low and levels of pituitary gonadotropins (LH and FSH) are elevated.

Testosterone may be indicated for replacement therapy in males in conditions associated with symptoms of deficiency or absence of endogenous testosterone such as: Primary hypogonadism (congenital or acquired)-testicular failure due to cryptorchidism, bilateral torsion, orchitis, vanishing testis syndrome; and hypogonadotropic hypogonadism (congenital or acquired)-idiopathic gonadotropin or LHRH deficiency, or pituitary-hypothalamic injury from tumors, trauma, or radiation, among others.

When used within the context of the present disclosure, the term "testosterone" may be taken to encompass any androgenic steroid that is functional in treatment of testosterone deficiency.

Amount of testosterone cypionate in disclosed TBIS may be of about 5% weight by volume to about 20% weight by volume; most suitable amount may be of about 10% weight by volume to about 20% weight by volume.

Anastrozole

Anastrozole is a non-steroidal aromatase inhibitor and is chemically described as 1,3-benzenediacetonitrile,a,a,a',a'-tetramethyl-5-(1H-1,2,4-triazol-1-ylmethyl). The molecular formula of anastrozole is $C_{17}H_{19}N_5$.

Anastrazole acts by blocking the enzyme aromatase, subsequently limiting the amount of male hormones that are changed into estrogen by the aromatase enzyme, a process called aromatization.

Generally speaking, the primary use of anastrozole for men is to suppress the production of estrogen, the main female sex hormones. The suppression of estrogen, specifically the hormone estradiol, is often necessary for men who have hormone disorders. Elevated levels of the female hormone (estradiol) in men can be manifested in gynecomastia or growth of breasts in males and hypogonadism or the reduced function of the testes. Excess of estradiol can also contribute to increased risk of stroke, heart attack, chronic inflammation, prostate enlargement and prostate cancer. Prescribing anastrozole for men in these situations has shown significant decrease of estradiol levels and, therefore, a decrease in symptoms and risks.

Furthermore, anastrozole has the ability to increase testosterone in the body. Some studies have shown that natural testosterone levels have increased as much as 60% for about 7 days after the single dose of anastrozole. Study data also suggests dosages of 0.5 mg to 1 mg a day may reduce approximately 50% of serum estradiol in men.

Additionally, the use of anastrozole may decrease fat mass, which can also be tied to estrogen levels.

Amount of anastrozole in disclosed TBIS may be of about 0.005% weight by volume to about 0.5% weight by volume; most suitable amount may be of about 0.05% weight by volume to about 0.2% weight by volume.

Methods of Elaboration

TBIS may be produced by suspending or emulsifying APIs in suitable vegetable oil such as Almond oil, Corn oil, Cottonseed oil, Olive oil, Peanut oil, Sesame oil, Soybean oil, and medium chain triglycerides (or caprylic capric triglycerides), among others. Additionally, other suitable solvents such as Benzyl Alcohol and Benzyl Benzoate may be added. TBIS may then be packed in suitable packages. Appropriate aseptic procedures must be observed through the entire process, and suitable sterilization must be done.

In other embodiments, TBIS may be produced into an aqueous injection together with, for example, surfactants, dispersing agent, suspending agents, preservatives, and tonicity adjusting agent, among others.

Application

Disclosed TBIS may be used to deliver an appropriate level of testosterone and anastrozole to achieve a suitable bloodstream level of testosterone.

The synergistic effect between testosterone and anastrozole may lead to increased levels of testosterone in the patient; therefore, TBIS may be used in treating a wide variety of conditions responsive to testosterone deficiency.

In one embodiment, TBIS may be injected to restore testosterone and maintain testicular function. Furthermore, TBIS may be administered to a patient that suffers from prostate cancer or to a patient that suffers from a disorder related to male hypogonadism.

In other embodiments, TBIS may be administered to a patient that is in need of increased muscle mass. TBIS may also be administered to a patient that suffers from lipodystrophy and to a patient that is in need of increased lymphocyte levels. TBIS may also be administered to a patient in need of reduced triglyceride level or to a patient that suffers from benign prostate hypertrophy.

Disclosed TBIS is an intramuscular injection. The therapeutic dosage and protocol varies, according to the individual person. Different formulations may be designed to provide higher or lower testosterone doses.

TBIS may be administered to a patient in weekly doses that results in a pharmacologically effective blood concentration of testosterone over a suitable period of time. The dosage may be of from about 25 mg/week to about 500 mg/week of testosterone; and of from about 0.1 mg/week to about 5 mg/week of anastrozole. Most suitable dosage may be of from about 50 mg/week to about 100 mg/week of testosterone; and of from about 0.1 mg/week to about 5 mg/week of anastrozole. In one embodiment, TBIS may be injected for an undetermined extended period of time. In other embodiments, TBIS may be injected as prescribed by a doctor, according to the patient's need.

In another aspect of the disclosure, pharmaceutical compositions including synergistic combination of testosterone with anastrozole, including suitable vehicles, may include other dosage forms such as oral capsules, sublingual drops, tablet triturates or troches, and topical compositions, among others.

EXAMPLES

Example #1 is an embodiment for formulation of TBIS which includes the ingredients described in table 1:

TABLE 1

| Example #1 TBIS formulation | |
|---|---|
| Ingredients | Percentages (W/V) |
| Testosterone cypionate | 5-20 |
| Anastrozole | 0.005-0.5 |
| Benzyl Benzoate | up to 46 |
| Benzyl Alcohol | up to 10 |
| Cottonseed Oil | q.s. to 100 |

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. An aqueous injection for increasing hormone levels comprising testosterone cypionate, 0.05% to 0.2% weight by volume anastrozole, caprylic capric triglyceride and a vegetable oil selected from the group consisting of almond oil, corn oil, cottonseed oil, olive oil, peanut oil, sesame oil, soybean oil, and combinations thereof.

2. The composition according to claim 1, further comprising at least one solvent.

3. The composition according to claim 2, wherein the at least one solvent is selected from benzyl alcohol, benzyl benzoate, and combinations thereof.

4. The composition according to claim 1, wherein the pharmaceutical composition is a suspension.

5. The composition of claim 1, wherein the testosterone cypionate and the anastrozole are emulsified in the caprylic capric triglyceride and the vegetable oil.

6. An aqueous solution for increasing hormone levels consisting essentially of 5% to 20% weight by volume testosterone cypionate, 0.05% to 0.2% weight by volume anastrozole, cottonseed oil, and at least one from the group consisting of benzyl benzoate and benzyl alcohol.

* * * * *